US012330343B2

(12) United States Patent
Dubois

(10) Patent No.: US 12,330,343 B2
(45) Date of Patent: Jun. 17, 2025

(54) PROCESS FOR JOINT RECYCLING OF COMPOSITE ITEMS BASED ON A THERMOPLASTIC POLYMER MATRIX

(71) Applicant: Arkema France, Colombes (FR)

(72) Inventor: Jean-Luc Dubois, Colombes (FR)

(73) Assignee: Arkema France, Puteaux (FR)

( * ) Notice: Subject to any disclaimer, the term of this patent is extended or adjusted under 35 U.S.C. 154(b) by 638 days.

(21) Appl. No.: 17/642,369

(22) PCT Filed: Sep. 25, 2020

(86) PCT No.: PCT/FR2020/051677
§ 371 (c)(1),
(2) Date: Mar. 11, 2022

(87) PCT Pub. No.: WO2021/058923
PCT Pub. Date: Apr. 1, 2021

(65) Prior Publication Data
US 2022/0324140 A1    Oct. 13, 2022

(30) Foreign Application Priority Data
Sep. 26, 2019 (FR) ...................... 1910659

(51) Int. Cl.
*C07C 67/00* (2006.01)
*B29B 13/10* (2006.01)
*B29B 17/02* (2006.01)
*B29K 33/00* (2006.01)
*B29K 105/00* (2006.01)

(52) U.S. Cl.
CPC .......... *B29B 17/0206* (2013.01); *B29B 13/10* (2013.01); *C07C 67/00* (2013.01); *B29B 2017/0224* (2013.01); *B29B 2017/0258* (2013.01); *B29K 2033/12* (2013.01); *B29K 2105/0002* (2013.01)

(58) Field of Classification Search
USPC .......................................................... 521/43
See application file for complete search history.

(56) References Cited

U.S. PATENT DOCUMENTS 5,536,831 A * 7/1996 Kopietz ............... C07D 201/12
540/485
6,469,203 B1   10/2002 Weiss et al.

FOREIGN PATENT DOCUMENTS

| BR | 102012003417 A2 * | 4/2014 | ............ B29B 17/02 |
| DE | 19843112 A1 | 4/2000 | |
| EP | 0522235 A1 | 1/1993 | |
| WO | WO-9618612 A1 * | 6/1996 | .......... C07D 201/12 |
| WO | WO-2013056845 A2 * | 4/2013 | ............ B29C 70/44 |
| WO | 2014135815 A1 | 9/2014 | |
| WO | WO-2014202730 A1 * | 12/2014 | ............ B29B 17/02 |
| WO | 2015177580 A2 | 11/2015 | |

OTHER PUBLICATIONS

Hawkins, W. Lincoln. "Polymer degradation." Polymer degradation and stabilization. Berlin, Heidelberg: Springer Berlin Heidelberg, 1984. 3-34, (Year: 1984).*
H. S. Wang, N. P. Truong, Z. Pei, M. L. Coote and A. Anastasaki, Reversing RAFT Polymerization: Near-Quantitative Monomer Generation Via a Catalyst-Free Depolymerization Approach, J. Am. Chem. Soc., 2022, 144(10), 4678-4684 (Year: 2022).*
WO-2014202730-A1 Machine Translation (Year: 2014).*
BR-102012003417-A2 (Year: 2014).*
International Search Report (PCT/ISA/210) with English translation and Written Opinion (PCT/ISA/237) mailed on May 11, 2021, by the European Patent Office as the International Searching Authority for International Application No. PCT/FR2020/051677.

* cited by examiner

*Primary Examiner* — Terressa Boykin
(74) *Attorney, Agent, or Firm* — Buchanan Ingersoll & Rooney PC

(57) ABSTRACT

A process for recycling a first article to be recycled including a composite material based on a fibrous reinforcer and a thermoplastic, preferably (meth)acrylic, polymer matrix, wherein the recycling process includes the following steps: introduction of the first article into a system suitable for the recycling of thermoplastic polymer, introduction, into the system suitable for the recycling of thermoplastic polymer, of a second article to be recycled including a thermoplastic polymer resin, and not including any fibrous reinforcer, heating of the articles to be recycled at a given temperature, in the system suitable for recycling thermoplastic polymer, so as to depolymerize the thermoplastic, preferably (meth)acrylic, polymers, and to form base monomers of the thermoplastic polymers, and recovery of the constituent base monomers of the thermoplastic polymers.

22 Claims, 5 Drawing Sheets

PROCESS FOR JOINT RECYCLING OF COMPOSITE ITEMS BASED ON A THERMOPLASTIC POLYMER MATRIX

TECHNICAL FIELD

The present invention relates in general to the recycling of articles made of composite material based on thermoplastic polymer matrix and in particular to a process for recycling articles made of composite material based on a fibrous reinforcer and thermoplastic polymer matrix, notably such as a (meth)acrylic thermoplastic polymer. The invention also relates to a system for recycling articles made of composite material which can implement such a process.

The invention is useful in all industrial sectors confronted with the problems of recycling of post-consumer composite waste having a thermoplastic polymer matrix, notably a (meth)acrylic thermoplastic polymer matrix, such as end-of-life products, or industrial waste such as defective products or scraps originating from plastic processing operations.

PRIOR ART

Composite materials are widely used in various industrial sectors: transportation (motor vehicle, railway), sports and leisure, health, wind power, nautical or aeronautical sectors. These composite materials (also abbreviated to "composites") are a macroscopic combination of at least two materials which are mutually immiscible. Generally, the composite material is composed of a polymer matrix which forms a continuous phase on the one hand, and of a reinforcing material (or reinforcement) which is generally a fibrous reinforcement on the other hand. There are also composites consisting of a polymer matrix and mineral filler, for example quartz, marble, silica, aluminum hydroxide or titanium dioxide. Optionally, the composite material also comprises additives. These materials are furthermore often combined with other components such as metal inserts, wood or foams in order to manufacture articles intended for various industries. Their recycling is a major challenge in a context of transition toward a circular economy for efficient use of resources and reduction of the environmental impacts of products throughout their life cycle.

The recycling of articles comprising a composite based on a polymer matrix or polymer composite can be performed according to several methods. These methods generally involve the thermal degradation of the polymer, i.e. a rise in temperature of the polymer causes the loss of the mechanical and physical properties of the polymer, followed by its depolymerization.

Pyrolysis is known, which is a thermal process consisting in placing the article to be treated in a suitable chamber and then heating the chamber so that the heat is transferred to the article. The pyrolysis temperature is generally between 400° C. and 1300° C. in order to enable the chemical decomposition of the polymer matrix. Pyrolysis of the article leads to the formation of gas, an oily residue and a solid residue comprising the reinforcement of the composite, inorganic fillers and a carbonaceous solid. The gases obtained after pyrolysis can be exploited in the manufacture of new polymer articles, and the solid residue obtained after pyrolysis is notably exploited in the manufacture of other products such as insulation materials. This recycling method generally has a mediocre yield of monomer (e.g. methyl methacrylate). Specifically, it is well known from the literature that composite materials lead, during pyrolysis, to the formation of more residues and to poorer yields of monomers than the pure polymer.

Fluidized bed processes are also known in which the fluidized bed can be a bed of silica sand, for example. In this process, the article comprising a composite is generally preground and is placed in a fluidized bed reactor containing the fluidized bed. Fluidization is performed using a gas stream heated at a temperature generally above 400° C. In this bed, the matrix is rapidly heated and gasified, thus removing the reinforcer from the matrix. A portion of the reinforcer is then carried out of the bed in the gas stream to a secondary combustion chamber. Another portion is entrained with the solid constituting the fluidized bed, and taken into a vessel where the solid is reheated, and the carbonaceous residues burnt before being returned to the fluidized bed reactor. As with pyrolysis, this method is not designed to optimize the yield of monomer.

In particular, poly(methyl methacrylate) (PMMA) is a well-established thermoplastic polymer known for its optical properties. Sold, for example, under the name Altuglas®, about 300 000 tonnes of PMMA are produced annually in Europe. Although PMMA can be converted into monomer by thermal depolymerization, only about 30 000 tonnes of PMMA waste are collected for recycling each year in Europe. In addition, to a large extent, the recycling of PMMA in Europe is currently based on a lead process (molten lead bed) which does not make it possible to retreat the inferior grades of PMMA (e.g. in the form of composites or highly additivated) since these inferior grades lead to the formation of a large amount of residues and to poor yields of monomers.

It is seen that the known methods for recycling articles comprising a composite material involve various heating steps which do not allow, in particular in the presence of a fibrous composite, a formation of monomers in high yields.

Consequently, from an energetic and environmental viewpoint, it is desirable to have available a recycling method which can improve the yield of monomer formation during the recycling of fibrous composites based on thermoplastic, for example (meth)acrylic, polymer matrix.

TECHNICAL PROBLEM

The aim of the invention is to overcome the drawbacks of the prior art. The invention is notably directed toward proposing a simple and efficient solution for depolymerizing a constituent polymer of an article made of composite material based on a fibrous reinforcer.

BRIEF DESCRIPTION OF THE INVENTION

To this end, the invention relates to a process for recycling a first article to be recycled including a composite material based on a fibrous reinforcer and a thermoplastic, preferably (meth)acrylic, polymer matrix, characterized in that said recycling process comprises the following steps:
  introduction of the first article to be recycled into a system suitable for the recycling of thermoplastic polymer,
  introduction, into the system suitable for the recycling of thermoplastic polymer, of a second article to be recycled including a thermoplastic, preferably (meth)acrylic, polymer resin, and not including any fibrous reinforcer,
  heating of the articles to be recycled at a given temperature, in said system suitable for recycling thermoplastic polymer, so as to depolymerize the thermoplastic polymers, preferably (meth)acrylic polymers, and to form base monomers of said thermoplastic polymers, and recovery of the constituent base monomers of said thermoplastic polymers.

As will be detailed hereinbelow and in the examples, such a process makes it possible to improve the base monomer production yield.

According to other optional features of the process:

It comprises a step of purifying the base monomers recovered beforehand. Specifically, given that the thermoplastic polymers of the first and second articles to be recycled may be different, the process according to the invention may lead to the production of a wide variety of monomers that will be able to be separated during a purification step, for example distillation. Specifically, although the first and second articles to be recycled each include a polymer, preferably a (meth)acrylic polymer, they may include different comonomers and different additives.

It comprises a step of removing the solid components produced during the step of heating the first and second articles to be recycled. Considering the presence of fibrous reinforcers and optionally of fillers, this makes it possible to free the recycling system of solid material that might harm the performance in particular in the context of a continuous recycling system.

The thermoplastic polymer matrix of the first article is a poly(methyl methacrylate) matrix. Poly(methyl methacrylate), which can be depolymerized to methyl methacrylate (MMA), is particularly suitable for the process according to the invention.

The first article to be recycled and the second article to be recycled are introduced in a mass ratio of between 0.1 and 1.5, preferably in a mass ratio of between 0.1 and 0.5, more preferably in a mass ratio of between 0.2 and 0.4. As presented in the examples, such ratios allow a significant improvement in the yields.

The first article to be recycled has a mass percentage of fibrous reinforcer of greater than 30%, preferably greater than 50%, more preferably greater than 70%. The higher the mass percentage of fibrous reinforcer in the article to be recycled, the lower the base monomer recovery yield usually is. Nevertheless, under these low yield conditions, the gains permitted by the process according to the invention are high. Thus, whereas this type of material is very difficult to recycle via conventional techniques, the process according to the invention has a marked advantage. In particular, the mass percentage of fibrous reinforcer corresponds here to the mass of fibrous reinforcer in the first article to be recycled relative to the total mass of the first article to be recycled.

The second article to be recycled is in the form of a syrup at room temperature (e.g. 25° C.) and has a mass percentage of equivalent thermoplastic monomer, preferably of (meth)acrylic monomer, of greater than 80%, preferably greater than 90%, preferably greater than 95%.

In another embodiment, the second article to be recycled has a mass percentage of equivalent thermoplastic monomer, preferably of (meth)acrylic monomer, of less than 95%, preferentially less than 90%, preferably less than 80%, more preferably less than 70%. Specifically, although the invention can function with cast plates of substantially pure methacrylic thermoplastic polymer, the invention allows a higher gain in combined base monomer recovery yield when the second article has reinforcers, additives or fillers, without substantial degradation of the purity.

In another embodiment, the second article to be recycled has a mass percentage of equivalent methyl methacrylate monomer of less than 95%, preferentially less than 90%, preferably less than 80%, more preferably less than 70%. As previously, the invention allows a higher gain in combined base monomer recovery yield when the second article has polymers or copolymers which are not based on methyl methacrylate. This is particularly advantageous when the thermoplastic polymer matrix of the first article to be recycled is PMMA.

The system suitable for the recycling of thermoplastic polymer is selected from:
an extruder and/or conveyor depolymerization system, a rotating drum depolymerization system, and
a system of depolymerization on heating plates, preferably continuously.

during the heating step, the first and second articles to be recycled are heated to a temperature of between 200° C. and 1500° C., preferably to a temperature of between 200° C. and 600° C. and advantageously to a temperature of between 300° C. and 600° C.

it also includes moderate heating of the thermoplastic polymers, preferably (meth)acrylic polymers, so as to at least partially liquefy them. Such moderate heating allows liquefaction but no depolymerization. During moderate heating, thermoplastic polymers, preferably (meth)acrylic polymers, are heated to a temperature of between 200° C. and 350° C., preferably to a temperature of between 200° C. and 325° C. and advantageously to a temperature of between 225° C. and 300° C. It may be performed at a temperature substantially equal to 270° C.; such a temperature must be sufficient to allow the movement of the liquefied thermoplastic polymers. The moderate heating may be moderate heating of the second article or moderate heating of the second article and of the first article to be recycled. Performing moderate heating may allow an improvement in the yield gains.

recovery of the fibrous reinforcer of the first article to be recycled, said recovery being performed by at least one of the following processes: centrifugation, draining, spinning, pressing, filtering, screening and/or cycloning. During the heating of the article to be recycled including a fibrous reinforcer, it is possible to separate the polymer matrix from said article so as to recover the fibrous reinforcer so as to increase the degree of purity of the monomers recovered thereafter and optionally to reuse the fibrous reinforcer without it being degraded.

To this end, the invention relates to a process for recycling a first article to be recycled including a composite material based on a fibrous reinforcer and a thermoplastic, preferably (meth)acrylic, polymer matrix, characterized in that said recycling process comprises the following steps:

a means for conveying said first article to be recycled,
a means for conveying a second article to be recycled including a thermoplastic, preferably (meth)acrylic, polymer resin, and not including any fibrous reinforcer, and
a reactor suitable for heating the articles to be recycled and for the depolymerization of the thermoplastic polymers, preferably (meth)acrylic polymers, and the formation of base monomers of said thermoplastic polymers.

Advantageously, but without being limiting, a recycling system according to the invention comprises a second reactor suitable for moderate heating of one of the articles to be recycled, preferably of the second article to be recycled, said second reactor comprising an aperture arranged to be in fluid communication with the first reactor.

In a particular embodiment, a recycling system according to the invention comprises a means for recovering constituent base monomers of the thermoplastic polymers.

In a preferred embodiment, a recycling system according to the invention comprises a means for placing in motion said first and second articles to be recycled.

Other advantages and features of the invention will become apparent on reading the following description given as an illustrative and nonlimiting example, with reference to the appended figures.

Figure 1:
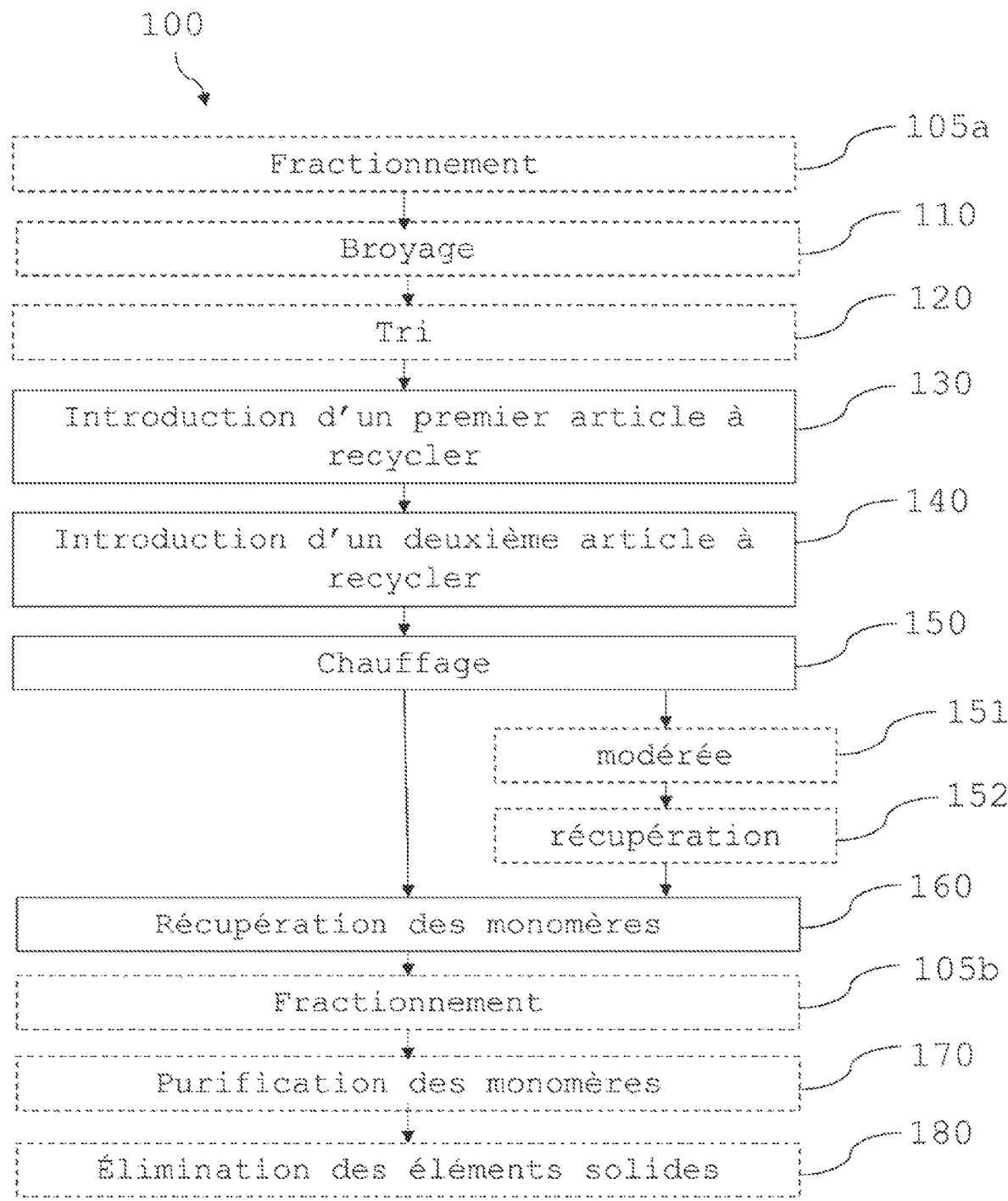
FIG. 1 represents a step diagram of the recycling process according to one embodiment of the invention.

Aspects of the present invention are described with reference to flow charts and/or block diagrams of processes or systems (or devices) according to embodiments of the invention. In the figures, the flow charts and the block diagrams illustrate the architecture, the functionality and the functioning of possible implementations of systems and of processes according to various embodiments of the present invention. In this regard, each block in the flowcharts or block diagrams may represent a system, a device or a module for performing the specified logic function(s). In certain implementations, the functions associated with the blocks may appear in an order different from that which is indicated in the figures. For example, two blocks shown successively may, in fact, be performed substantially simultaneously, or the blocks may occasionally be performed in the reverse order, depending on the functionality involved.

DESCRIPTION OF THE INVENTION

In the remainder of the description, the term "monomer" means a molecule which can undergo polymerization.

The term "polymerization" as used relates to the process for converting a monomer or a mixture of monomers into a polymer.

The term "polymer" means either a copolymer or a homopolymer. A "copolymer" is a polymer grouping together several different monomer units and a "homopolymer" is a polymer grouping together identical monomer units.

The term "depolymerization" as used relates to the process for converting a polymer into one or more monomers and/or oligomers and/or polymers of smaller molecular mass relative to the molecular mass of the initial polymer.

The term "base monomer" means the most predominant monomer unit constituting a polymer. Thus, in PMMA, the base monomer is MMA.

The term "thermoplastic polymer" or "thermoplastic" means a polymer which, in a repeated manner, can be softened or melted under the action of heat and which takes on new shapes by application of heat and pressure. Examples of thermoplastics are, for example: high-density polyethylene (HDPE) notably used for the production of plastic bags or for motor vehicle construction; polyethylene terephthalate (PET) or polyvinyl chloride (PVC) which are notably used for the production of plastic bottles; polystyrene (PS) used in the packaging and construction sectors; polymethyl methacrylate PMMA). Thus, the use of thermoplastics affects a wide variety of sectors, ranging from packaging to the motor vehicle industry, and the demand for plastics remains high.

The term "thermoplastic monomer" means the monomer(s) or molecule(s) which, after polymerization, are in the chain of a thermoplastic polymer.

The term "(meth)acrylic thermoplastic polymer" or "(meth)acrylic polymer" means a homopolymer or a copolymer based on (meth)acrylic monomer, which is chosen, for example, from methyl methacrylate, ethyl methacrylate, methyl acrylate, ethyl acrylate, methacrylic acid, acrylic acid, n-butyl acrylate, isobutyl acrylate, n-butyl methacrylate, isobutyl methacrylate, cyclohexyl acrylate, cyclohexyl methacrylate, isobornyl acrylate, isobornyl methacrylate and mixtures thereof. Poly(methyl methacrylate) (PMMA) is a particular example of a (methacrylic) polymer obtained by polymerization of a methyl methacrylate monomer.

For the purposes of the invention, the term "PMMA" denotes homopolymers and copolymers of methyl methacrylate (MMA), the weight ratio of MMA in the PMMA preferably being at least 70% by weight for the MMA copolymer. The term "copolymer based on methyl methacrylate" means a copolymer containing at least one methyl methacrylate monomer. For example, a copolymer based on methyl methacrylate may be a copolymer comprising at least 70%, preferably 80%, advantageously 90% by weight of MMA in the PMMA.

The term "polymer matrix" means a polymer-based solid material which serves as binder in the context of a composite material. The "matrix" includes polymers and/or oligomers and may also include additives and/or fillers. Thus, a "(meth)acrylic polymer matrix" relates to any type of matrix including acrylic and methacrylic polymers, oligomers or copolymers. However, it would not constitute a departure from the scope of the invention if the (meth)acrylic polymer matrix comprised up to 49% by weight, preferably less than 40% by weight, of nonacrylic compounds, for example in the form of monomers, polymers, copolymers or block copolymers chosen, for example, from the following group: lactic acid, butadiene, isoprene, styrene, substituted styrene, such as α-methylstyrene or tert-butylstyrene, cyclosiloxanes, vinylnaphthalenes and vinylpyridines.

For the purposes of the invention, the term "polymer resin" corresponds to a polymer-based solid material. The "polymer resin" includes polymers and/or oligomers and may also include additives and/or fillers. The polymer resin may be in solid or liquid form (notably in the form of a syrup). The additives and/or fillers may in particular improve certain properties such as the impact strength or the heat resistance. Thus, a "(meth)acrylic polymer resin" relates to any type of resin including acrylic and methacrylic polymers, oligomers or copolymers. However, it would not constitute a departure from the scope of the invention if the (meth)acrylic polymer resin comprised up to 49% by weight, preferably less than 40% by weight, of nonacrylic compounds, for example in the form of monomers, polymers, copolymers or block copolymers chosen, for example, from the following group: methacrylonitrile, lactic acid, butadiene, isoprene, styrene, substituted styrene, such as α-methylstyrene or tert-butylstyrene, cyclosiloxanes, vinylnaphthalenes and vinylpyridines.

For the purposes of the invention, the term "syrup" refers to a liquid composition with a dynamic viscosity of between 10 mPa·s and 10 000 mPa·s at 25° C. The dynamic viscosity of the syrup is in a range from 10 mPa·s to 10 000 mPa·s, preferably from 20 mPa·s to 7000 mPa·s, and advantageously from 20 mPa·s to 5000 mPa·s. The viscosity of the syrup may be readily measured with a rheometer or a viscometer. The dynamic viscosity is measured at 25° C.

For the purposes of the invention, the term "composite" means a multi-component material comprising at least two immiscible components, in which at least one component is a polymer and the other component may be, for example, a reinforcer such as a fibrous reinforcer or fillers.

The term "reinforcer" means a non-depolymerizable or gasifiable solid material such as a "fibrous reinforcer" or a "mineral filler" which generally remain at the end of recycling.

The term "fibrous reinforcer" means an assembly of fibers, unidirectional rovings or a continuous filament mat, fabrics, felts or nonwovens which may be in the form of strips, webs, braids, strands or parts. In the context of the invention, a fibrous reinforcer will preferably correspond to a reinforcer including fibers greater than 10 mm, more preferably greater than 20 mm and even more preferably greater than 3 cm in length.

The term "mineral fillers" means all pulverulent fillers, for example quartz, marble, silica, aluminum hydroxide or titanium dioxide.

For the purposes of the invention, the term "mass ratio" corresponds to a ratio relative to the weights of the articles to be recycled.

For the purposes of the invention, the term "mass percentage of equivalent methacrylic monomer" corresponds to a theoretical mass content of methacrylic monomer relative to the total weight of the article to be recycled. This percentage is preferably calculated without taking into account any methacrylic fraction that might be contained in fillers or additives present in the mass of the article. A theoretical mass of methacrylic monomer may correspond to a mass fraction originating from methacrylic monomers in a polymer or a copolymer.

For the purposes of the invention, the expression "at least partially liquefying the thermoplastic polymers" corresponds to the initiation of a step of at least partial melting (i.e. largely exceeding the glass transition temperature $T_g$ and/or the melting point $T_m$, the latter only being for a crystalline or semicrystalline polymer) of the thermoplastic polymers contained in the articles to be recycled. Depending on the polymers considered, the temperature must enable the molten thermoplastic polymer to have a viscosity sufficient to allow the extrusion of the polymer without totally decomposing it.

For the purposes of the invention, the term "substantially equal" means a value varying by less than 30% relative to the compared value, preferably by less than 20%, even more preferably by less than 10%.

In the following description of the embodiments and in the appended figures, the same references are used to denote the same components or similar components.

The recycling of the materials and more so of the composite materials requires numerous parameters to be taken into account in order for the recycling to have a carbon footprint and an energy footprint that are more favorable than the energy footprint of the initial manufacture.

In particular, for the recycling of composite materials with a thermoplastic, preferably (meth)acrylic, polymer matrix, the technical problem to be solved is that of increasing the productivity during the depolymerization of composites with a (meth)acrylic thermoplastic polymer matrix. Specifically, the solutions conventionally provided consist in increasing the depolymerization temperature. However, in the case of a (meth)acrylic thermoplastic polymer matrix, increasing the temperature has little effect on the rate of depolymerization.

Surprisingly, the inventor has discovered that when composites and different grades of thermoplastic polymer matrix, advantageously but in a nonlimiting manner (meth) acrylic matrix, are mixed, the yield of monomer obtained within a given time period is improved. This means that the yield is higher than it would have been by depolymerizing the two fractions independently over this same time period.

Thus, the inventor has developed a process for recycling composite materials based on thermoplastic, preferably (meth)acrylic, polymer matrix, having an improved yield of monomer. As will be presented in the examples, the gain in yield is all the more pronounced for certain mass ratios between the composite and the other grades of thermoplastic, preferably (meth)acrylic, polymer matrix. In addition, a recycling system which can perform such a process is also proposed.

The present invention makes it possible to obtain a satisfactory production of methyl methacrylate in particular starting with materials based on (meth)acrylate matrix that are sparingly recyclable (i.e. which have a low methyl methacrylate production yield).

The present invention thus notably relates to a process for recycling an article made of composite material. The article made of composite material, or first article 10 to be recycled, may notably be an article made of composite material based on a fibrous reinforcer and a thermoplastic polymer matrix, preferably a (meth)acrylic thermoplastic polymer matrix. In particular, it should be noted that the article to be recycled may be a manufactured product or part of a manufactured product at the end of its life, or waste from the production of such a product. In both cases, a prior sorting step may prove necessary in order to eliminate non-depolymerizable waste or any non-depolymerizable product also contributing to losses in energy efficiency.

The article made of composite material, or first article 10 to be recycled, may also include other polymers besides the thermoplastic polymer matrix of the composite material based on a fibrous reinforcer. This may be adhesive, foam, gel coat or other polymers different in nature from the thermoplastic polymer matrix of the composite material. In this case, a fractionation step 105 may prove to be necessary either upstream 105a or downstream 105b, so as to remove these other polymers or to reduce the amount of these other polymers. Preferably, the fractionation step 105, if it takes place, is performed upstream of the fractionation step 105b, more preferably before the grinding step 110.

As has been mentioned, the composite materials based on a fibrous reinforcer have yields of recycled monomers, whether on a molar or mass basis, which are lower than those of noncomposite materials (e.g. yields calculated after recovery of a condensate and separation of the base monomers on the basis of a theoretical content of base monomers). Now, the present technology is particularly suitable for such materials. A mass yield of recovered base monomer relative to the equivalent monomer may be calculated by taking into account the mass content of monomer recovered from the condensate and the theoretical mass content of monomer in the article to be recycled. However, such a calculation presupposes the possibility of determining the theoretical mass content of monomer in the recycled article. This is possible in certain controlled experiments but proves to be more difficult during the industrial use of the invention. Thus, in the examples, an improvement in the mass yield is mentioned. This is based on an increase in the mass of base monomer recovered using a process according to the invention in comparison with a mass of base monomer recovered by means of the techniques of the prior art.

In the composite material, the thermoplastic polymer matrix is intimately bound to the reinforcer. The fibrous reinforcer may be seen as a reinforcing means, often based on glass or carbon fibers. For example, the fibrous reinforcer may be a fabric, webs, felts or any other fibrous material. The fibrous reinforcer will be based, for example, on glass fiber, carbon fiber or basalt fiber, or alternatively metal or plant fibers.

The (meth)acrylic thermoplastic polymer may be a homopolymer or a copolymer based on (meth)acrylic monomer, which is chosen, for example, from methyl methacrylate, ethyl methacrylate, methyl acrylate, ethyl acrylate, methacrylic acid, acrylic acid, n-butyl acrylate, isobutyl acrylate, n-butyl methacrylate, isobutyl methacrylate, cyclohexyl acrylate, cyclohexyl methacrylate, isobornyl acrylate, isobornyl methacrylate and mixtures thereof.

In particular, the composite material of the article to be recycled is based on PMMA and fibrous reinforcer.

The main steps of a recycling process according to the invention are detailed in FIG. 1. In particular, a recycling process 100 according to the invention includes an introduction 130 of a first article 10 to be recycled into a system 1 suitable for the recycling of thermoplastic polymer, an introduction 140 into the system 1 of a second article 20 to be recycled including a thermoplastic, preferably (meth)acrylic, polymer resin, but not including any fibrous reinforcer, heating 150 of the articles to a given temperature and recovery 160 of the constituent base monomers of the thermoplastic, preferably (meth)acrylic, polymers. The second article 20 to be recycled may also contain additives to improve certain properties: for example the impact strength, the heat resistance. Generally, such additives may interfere with the depolymerization.

The second article to be recycled may also be in the form of a syrup at room temperature and have a mass percentage of equivalent thermoplastic monomer, preferably of (meth) acrylic monomer, of greater than 70%, for example greater than 75%, preferably greater than 80%, more preferably greater than 90% and even more preferably greater than 95%. Specifically, such a syrup is obtained either during the preparation of plates cast during the prepolymerization of methyl methacrylate, or by dissolution of PMMA in methyl methacrylate. Preferably, during the use of the second article, a polymerization-inhibiting additive is added to the second article. Such an additive may be hydroquinone, MEHQ (4-methoxyphenol), phenothiazine or topanol (2,4-dimethyl-6-tert-butylphenol). Such a syrup may advantageously, but without being limiting, consist of an Elium® resin in liquid form.

In addition, as will be detailed hereinbelow, a process 100 according to the invention may include steps of fractionation 105, grinding 110, sorting 120, purification 170 of the base monomers recovered beforehand, and removal 180 of the solid components produced during the heating step.

The present invention includes the joint recycling of two articles having different grades. In particular, a first article is a composite material including a fibrous reinforcer while a second article does not include any fibrous reinforcer.

In addition, as will be detailed hereinbelow, it is notably this combination of materials having different grades which allows the present invention to achieve monomer yields higher than the yields of these materials recycled separately. Thus, the present invention makes it possible to achieve correct monomer yields, i.e. yields at least higher than the yields of these materials recycled separately, from materials that are generally considered as being sparingly recyclable.

The grade system is a classification intrinsic to the industries specialized in the manufacture of materials and in particular of composite materials. This system makes it possible to reflect the quality of a material and, partly, its composition. Thus, the grade of a material will be influenced, for example, by:
- the presence or absence of a reinforcer, and the type of reinforcer used,
- the features of the matrix used: the polymer or the possible polymer combination forming the matrix, with, for example, the presence or absence of cross-linking, and
- the presence or absence of additives.

Thus, in the context of the present invention, the first article 10 to be recycled preferably has a first grade whereas the second article 20 to be recycled has a second grade different from the first grade.

In particular, the first article 10 to be recycled includes a fibrous reinforcer while the second article 20 to be recycled does not include any fibrous reinforcer.

The first article 10 to be recycled and the second article 20 to be recycled may include additives such as plastic additives, additives for improving the heat resistance, additives for improving the impact strength, comonomers, for example acrylates or other for blocking/slowing down the depolymerization. They may also include mineral fillers such as alumina, quartz, marble, aluminum hydroxide and titanium oxide. In particular, the thermoplastic polymer, which is preferably (meth)acrylic, may comprise at least one additive such as a stabilizer, a pigment, a plasticizer such as phthalates, an adhesion promoter, a UV absorber, an antioxidant, a flame retardant, a dye, a lubricant, a mold-release agent, a filler, an antistatic agent, a fungicide, a surfactant and/or crosslinked polymer beads, an impact strength additive, etc. Indeed, adding an additive generally makes it possible to enhance the properties of the thermoplastic composition. For example, the fillers improve the chemical or heat resistance, the plasticizers make it possible to reduce the stiffness, the stabilizers prevent degradation of the polymers, the antistatic agents prevent the deposition of dust, the lubricants limit the wear, the flame retardants offer better fire resistance, etc. Nevertheless, the presence of such additives usually heralds a low yield for the recovery of base monomer in the case of recycling by depolymerization.

Preferably, the second article 20 to be recycled includes at least 50 mass % of thermoplastic polymer, for example (meth)acrylic polymer, more preferably at least 60 mass % of thermoplastic polymer, for example (meth)acrylic polymer, and even more preferably at least 70 mass % of thermoplastic polymer, for example (meth)acrylic polymer.

In addition, the second article 20 to be recycled is advantageously not an article usually considered as being readily recyclable. Thus, it may preferably include at least 5 mass % of filler (such as a mineral filler), more preferably at least 10 mass % of filler and even more preferably at least 15 mass % of filler.

In a particular embodiment, the second article 20 to be recycled includes at least between 0.5 mass % and 25 mass % of acrylic or nonacrylic comonomer, preferably between 1 mass % and 10 mass %.

Preferably, the second article 20 to be recycled includes at least 5 mass % of additives relative to the total weight of thermoplastic composition, for example (meth)acrylic composition, preferably at least 10 mass %, more preferably at least 15 mass %.

Preferably, the second article 20 to be recycled includes up to 50 mass % of additives relative to the total weight of thermoplastic composition, for example (meth)acrylic composition, preferably less than 40 mass %, more preferably less than 30 mass % and even more preferably less than 25 mass %. Advantageously, but without being limiting, the second article 20 to be recycled includes up to 50 mass % of an additive such as an acrylic and/or methacrylate-butadiene-styrene impact modifier and/or acrylic processing agents, preferably up to 25%. The function of such an impact modifying additive is to improve the impact strength of thermoplastic materials. In a particular embodiment, the second article 20 to be recycled includes up to 30% of an additive of polylactic acid type. The additive of polylactic acid type is a thermoplastic resin derived from renewable plant resources and is certified compostable. Such a resin may also be associated with additives of impact modifier type.

In particular, the second article 20 to be recycled may include an at least partly crosslinked thermoplastic polymer resin.

As presented in FIG. 1, a recycling process 100 according to the invention may include a preliminary sorting step 120. The sorting step may be a step in which the first article 10 to be recycled comprising a composite material based on a fibrous reinforcer is separated and isolated. For example, it may be separated and isolated from articles not comprising any composite material, and/or it may be separated and isolated from contaminants such as glass, sand, wood, other polymers, foams or metals. The sorting step also allows the separation and sorting of plastics by family. For example, it is possible to sort the thermoplastic polymers on the one hand and the thermosetting polymers on the other hand, and also to sort various thermoplastics from each other. The sorting may also make it possible to eliminate portions resulting from the grinding which are not made of composite material.

The sorting may be performed by any sorting method suitable for polymer recycling. One possible sorting method may involve a decantation system in which the waste is placed in a tank of water and/or brine, or an organic liquid. The heavy components end up at the bottom of the tank, and can be discharged via a pneumatic airlock system. The components to be recycled may be extracted from the tank by means of an endless screw (at the top or at the bottom depending on their density). The sorting may also comprise magnetic sorting in order to extract metal particles. The sorting may also comprise eddy-current separation to remove certain metals such as copper and aluminum. It is also possible to combine separation technologies, such as sorting by density in a solution, and magnetic separation, for example. The sorting method may use spectroscopic technologies such as Raman or infrared, in order to recognize the composition of the materials. Sorting methods using the triboelectric properties of the materials or their hot adhesion properties may also be used. The sorting may be performed in a sorting center. The sorting step advantageously makes it possible to eliminate components which could damage the various devices used in the implementation of the recycling process 100.

In addition, for example in order to facilitate the introduction of the article into the reactor suitable for polymer recycling, the article may be ground beforehand. Thus, in one embodiment, the process 100 for recycling the article comprises a step 110 of grinding the article, performed before step 120 of FIG. 1, and, in this instance, it is more a case of crushing than of fine grinding since the sorting operations are thereby facilitated. The grinding step makes it possible to reduce the dimensions of the article to be recycled (the first and/or the second) and may be performed, for example, using any suitable mechanical grinder. Contactless grinding technologies may also be used. The first and second articles to be recycled are reduced to dimensions permitting the introduction of the ground material thus obtained into a device suitable for the recycling according to the invention. The particles obtained after grinding may, for example, have dimensions (e.g. radius, diameter, median diameter, length, width, height) such that at least one dimension is between 1 mm and 100 mm, preferably between 3 mm and 50 mm. Preferably, at least one of the dimensions of the second article 20 to be recycled is less than 30 mm. The first and second articles to be recycled may then take the form of chips, granules or powder. More preferably, the grinding is performed so that the second article to be recycled has at least one of its dimensions smaller than the largest dimension of the first article to be recycled. The first and second articles to be recycled may also be in the reactor in one or more of the abovementioned forms. Advantageously, the grinding/crushing step 110 may make it possible to facilitate a sorting step. It is, however, generally easier to sort large-sized pieces, on condition that their composition is homogeneous. The grinding operation thus also serves to create pieces of homogeneous composition. This is why it may be performed before the sorting operations described above. The grinding operation could also be selective grinding.

As illustrated in FIG. 1, a recycling process 100 according to the invention includes a step of introduction 140 of the first article 10 into a system 1 suitable for the recycling of thermoplastic polymer. In particular, the first article 10 may be introduced into a reactor that is suitable for polymer recycling.

For example, the first article 10 to be recycled may be introduced into the reactor by means of an endless screw, a conveyor belt, a hopper or by a metering module. The flow rate for feeding the reactor with a first article 10 to be recycled may be between 10 kg/h and 2000 kg/h, and preferably between 50 kg/h and 500 kg/h, preferably between 100 kg/h and 400 kg/h.

A recycling process 100 according to the invention also includes a step of introduction 120 of a second article 20 to be recycled into the system 1 suitable for the recycling of thermoplastic polymer.

The first article 10 and the second article 20 may be introduced successively or simultaneously into the system and in particular into a depolymerization reactor. Thus, the second article 20 to be recycled not including any fibrous reinforcer may be introduced before the first article 10 to be recycled.

Alternatively, the first article 10 and the second article 20 may have been mixed and introduced simultaneously into the recycling system 1 and in particular into a reactor suitable for polymer recycling. The first and second articles 10, 20, introduced, for example in the form of granules, chips, needles, platelets or powders, have a substantially different particle size. Advantageously, the article 10 to be recycled has larger dimensions than the article 20 to be recycled. The process 100 may also include the introduction of several other articles including a thermoplastic polymer, preferably a (meth)acrylic thermoplastic polymer.

Preferably, the first article 10 to be recycled including a composite material based on a fibrous reinforcer and thermoplastic, advantageously (meth)acrylic, polymer matrix, and the second article(s) 20 to be recycled based on thermoplastic, preferably (meth)acrylic, polymer resin, without fibrous reinforcer are introduced in a (second article(s)/first article) mass ratio of between 0.1 and 1.5, preferably in a ratio of between 0.1 and 0.5 and more preferably in a ratio of between 0.2 and 0.4.

As presented in FIG. 1, a recycling process 100 according to the invention also includes a step 150 of heating the first and second articles 10, 20. The heating may in particular be performed in a reactor of a system 1 suitable for the recycling of thermoplastic polymer, preferably for the recycling of a composite article including thermoplastic polymers.

Preferably, the system 1 suitable for the recycling of thermoplastic polymer resin is selected from:
an extruder/conveyor depolymerization system,
a rotating drum depolymerization system, and
a system of depolymerization on heating plates, for example functioning continuously.

The heating is performed at a temperature which makes it possible to depolymerize the thermoplastic polymers, preferably (meth)acrylic polymers, and to form base monomers of the thermoplastic polymers of the first and second articles 10, 20.

In particular, the heating of the article is performed at a given temperature allowing the depolymerization of the thermoplastic polymer and the generation of a base monomer in gaseous form. The heating may be performed, for example, at a temperature of between 200° C. and 1500° C., preferably between 300 and 600° C., more preferably between 350 and 500° C. and even more preferably between 400 and 450° C. The heating may also be staged, with a first heating zone at a moderate temperature, followed by a second and last or a second and thus multiple heating zones at increasing temperature. The moderate temperature is preferably between 200 and 350° C., more preferably between 200 and 300° C.

In a preferred embodiment, the heating of the articles 10, 20 to be recycled is performed under an inert atmosphere, for example under vacuum, under nitrogen, under $CO_2$ or under argon or under an atmosphere that is substantially low in oxygen (for example having from 0.1% to 10% oxygen). Such an oxygen-depleted atmosphere may be obtained, for example, by recycling the combustion gases of the light effluents from the depolymerization unit.

Similarly, advantageously, a process 100 according to the invention for recycling of the article includes a step of moderate heating 151 of the first and/or second article to be recycled. More preferably, a recycling process 100 according to the invention includes a step of moderate heating 151 of the second article to be recycled. This step of moderate heating of the article(s) to be recycled may be performed before the introduction thereof into the reactor and, where appropriate, after grinding. The moderate heating may be performed using any suitable heating means. In one variant, it may be initiated in the reactor suitable for polymer depolymerization. The temperature at which the article is preheated may be 50° C. or more, for example 200° C. By means of moderate heating of the article(s) to be recycled, a portion of the polymer may be converted to the molten state or the liquid state and/or the depolymerization of the polymer matrix may be facilitated.

A recycling process 100 may lead to the destructuring of the polymer matrix and to its conversion, for example, into a mixture in molten or liquid form. Thus, the heating step 150 may incorporate a step 152 of recovering the fibrous reinforcer. Such a step of recovering a fibrous reinforcer may be performed during the heating step or once said step is complete. Notably, the step of recovering the fibrous reinforcer may take place once the recovery of the monomers has been performed.

As presented in FIG. 1, a recycling process 100 according to the invention also includes a step 160 of recovering the constituent base monomers of the thermoplastic polymers, preferably (meth)acrylic polymers.

Advantageously, a process 100 according to the invention may include a step of condensation of these base monomers from the gaseous state to the liquid state so as to obtain a solution including the base monomers.

Preferably, this condensation may be performed by bringing monomers in the gaseous state into contact with monomers in the liquid state. This contacting operation may be performed, for example, in a device of shower type, by spraying the monomers in the liquid state (i.e., cold monomers) into a chamber collecting the base monomers in the gaseous state (i.e. hot monomers). In this case, the device may comprise a means for introduction of a stabilizer, or polymerization inhibitor.

Furthermore, the condensation of the gas mixture may be performed in a fractionated manner and lead to cleaner fractions containing the base monomer, and less-clean fractions containing monomer and contaminants. This fraction containing contaminants may also be reintroduced into the reactor in order to enable better separation of the monomers contained in this fraction.

A recycling process 100 according to the invention may also include a step 170 of purifying the base monomers recovered beforehand.

The purification step 170 may include a step of separation by distillation, for example by means of a distillation column. The reason for this is that, during the depolymerization, impurities may be formed, which subsequently need to be removed.

A recycling process 100 according to the invention may also include a step 180 of removing the solid components produced during the step of heating the first and second articles 10, 20. The separation means for removing the solid components is adapted to the state of the matrix in the reactor or at the outlet of the reactor, i.e. depending on whether the matrix is converted into a mixture in the molten or liquid state, or is converted into a mixture in the gaseous state. In the case where the reinforcer is contained in a mixture in the molten or liquid state, the separation means can be any means allowing a solid/liquid separation, such as a grid, for example. The separation can also be performed by centrifugation using a centrifuge, or else by decantation, filtration, draining, spinning, pressing or screening. Preferably, the separation is performed by filtration in a molten medium, pressing or decantation. In the case where the matrix is gasified/depolymerized, the gas-phase separation means may comprise a cyclone or filters, for example. When filters are used, back pressure is applied periodically to loosen the solid that has accumulated at the filter. The solid cake is then recovered below the filter in a vessel provided for this purpose. It should be noted that, during the depolymerization of the matrix, polymer residues may remain on the reinforcer, and solid-phase separation of the solid residues may be performed, for example, by screening (glass fiber/carbonaceous powder separation, etc.). This removal step advantageously makes it possible to process the various types of solid residues that are formed during the depolymerization reaction, namely the solid residues entrained in the gaseous phase and the solid residues which remain compact, which will notably be found at the reactor outlet. The solid residues entrained in the gaseous phase potentially risk clogging the monomer condensation unit. These solid residues must thus be filtered in the gaseous phase (for example via a suitable separation means: cyclone, filters) or in the liquid phase after condensation, whereas the solid residues which emerge at the reactor outlet generally remain in the form of a solid mat which can be screened, for example to separate the various solid residues. The hot solid residues must/can be cooled, for example by direct contact with water. During this cooling step, the direct contact between the solid and the monomer must be limited to prevent said monomer from recondensing directly on the solid.

According to another aspect, the invention relates to a system 1 for recycling a first article 10 including a composite material based on a reinforcer and a thermoplastic, preferably (meth)acrylic, polymer matrix.

Figure 2:
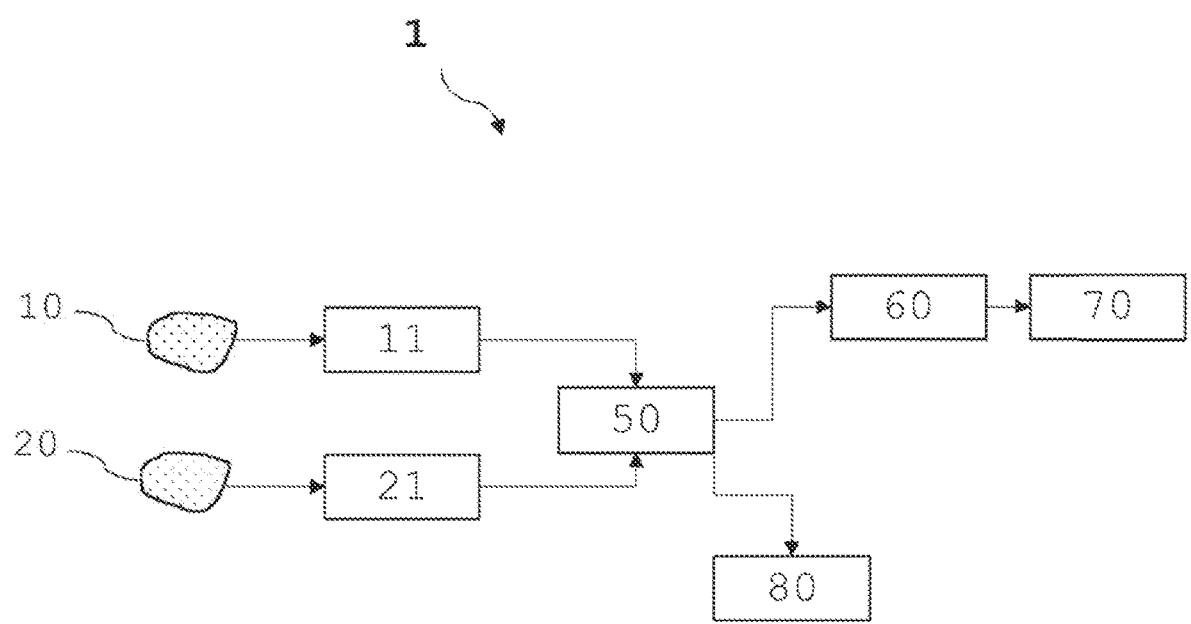
FIG. 2 represents an illustrative scheme showing an example of a recycling system according to one embodiment of the invention.

As illustrated schematically in FIG. 2, the recycling system 1 according to the invention comprises a means 11 for conveying a first article 10 including a composite material based on a fibrous reinforcer and a thermoplastic, for example a (meth)acrylate, polymer matrix, a means 21 for conveying a second article 20 to be recycled including a resin of a thermoplastic polymer, preferably a (meth)acrylic polymer. The conveying means 11, 21 may be a pipe, an endless screw, a conveyor belt or a hopper, a pneumatic transporter, a vibrating transporter or an extruder. In addition, they may be coupled to a metering device. The recycling system 1 according to the invention also comprises a reactor 50 suitable for heating the articles 10, 20 for the purpose of depolymerizing the thermoplastic polymers, preferably (meth)acrylic polymers, and of forming monomers. For example, the heating may be performed by exposure of the article to microwaves, to pulsed electric fields or to steam, or by contact with a hot surface as in an extruder, a screw conveyor, a rotating drum, etc. The hot surface may be heated by various means: direct electric heating, heating by heat-transfer fluid (steam, oil, molten salts, etc.).

The recycling system 1 according to the invention also comprises a means 60 for recovering constituent monomers of the thermoplastic polymers, which are advantageously, but without being limiting, (meth)acrylic polymers.

In addition, a recycling system 1 according to the invention may include one or more means for placing in motion the first 10 and second 20 articles to be recycled, one or more video acquisition means 356, described in connection with FIG. 4, such as an infrared camera, one or more purification means 70 and one or more solid removal means 80.

The reactor of a system 1 according to the invention may be an extruder or conveyor, a reactor suitable for pyrolysis, for high-temperature pyrolysis, for pyrolysis in a molten salt bath, or a fluidized bed reactor or a reactor suitable for solvolysis or else a reactor consisting of hollow plates heated by a heat-transfer fluid circulating in the plates. However, reactors enabling higher gains in monomer yield have been identified, such as: an extruder, a conveyor, an extruder-conveyor, a rotating drum and/or a set of heating plates.

A reactor suitable for recycling the thermoplastic polymer may also be a pyrolysis reactor, for example a multistage pyrolysis reactor or a stirred rotating cylinder reactor. Two configurations are possible: either the cylinder rotates on its axis, or an internal stirring system ensures mixing and heat transfer from the wall to the polymer.

An extruder-conveyor is a reactor comprising one or more endless screws each actuated in a barrel, notably allowing the blending of the components introduced into said barrel. The use of an extruder-conveyor for performing the recycling process 100 is advantageous from an environmental, security and safety viewpoint of the process 100. Specifically, an extruder-conveyor makes it possible to process molten polymers of high viscosity without the need to add solvent to reduce the viscosity of the molten polymers.

The extruder-conveyor has the advantage of allowing efficient heat transfer from the barrel to the composite to be treated. The extruder may advantageously be replaced with a screw conveyor system over all or part of the length thereof. Advantageously, the system may comprise the combination of a conveyor-type device in the first part, followed by an extruder-type device and terminated by a conveyor-type device configured to transport the solid (i.e. reinforcer) to the outlet. For example, the conveyor may be of the "auger screw" or "endless screw" type.

Figure 3:
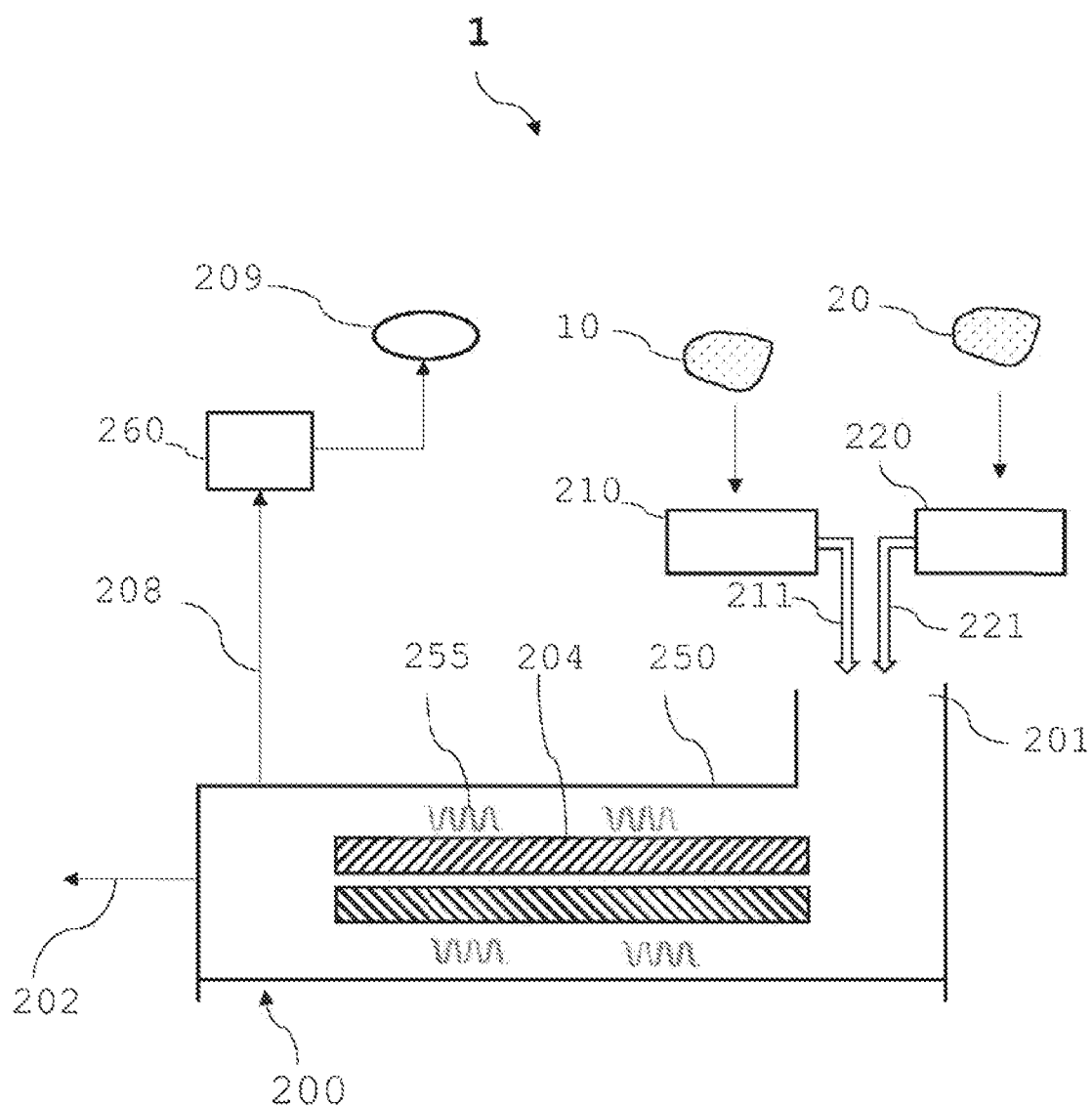
FIG. 3 represents a scheme of a side view in cross section showing an example of a recycling system including an extruder according to one embodiment of the invention.

With reference to FIG. 3, a recycling system 1 according to the invention may include an extruder, more particularly a twin-screw extruder 200 comprising an orifice 201 via which a first article 10 to be recycled comprising a composite material based on a fibrous reinforcer and a thermoplastic, preferably (meth)acrylate, polymer matrix, may be inserted, for example by means of a metering device 210 and a conveying means 211. Similarly, a second article to be recycled including a thermoplastic, preferably (meth)acrylic, polymer resin, may be inserted, for example by means of a metering device 220 and a conveying means 221. The first and second articles 10, 20 to be recycled may be in powder or granule form. Alternatively, the articles may be introduced into the extruder after having undergone a first heating step.

Thus, the first and second articles 10, 20 to be recycled are introduced hot or cold and may also be heated and/or maintained at temperature during the treatment.

A twin-screw extruder may be, for example, a Clextral® type extruder. The twin-screw extruder comprises two screws 204, which are usually parallel, rotating inside a barrel 250. Advantageously, the extruder is of modulable nature, i.e. the screw and the barrel 250 are modules assembled in series, and the assembly of which may be modified. Thus, the barrel 250 corresponds here to the reactor suitable for heating the articles 10, 20 for the purpose of depolymerizing the thermoplastic polymers, by way of nonlimiting example the (meth)acrylic polymers, of the recycling system 1 according to the invention. More generally, the reactor 50 of the system according to the invention may take various forms on condition that the gas streams and the temperature can be controlled.

In the extruder, an external heating means 255 regulating the temperature of the barrel 250 is advantageously configured to heat the first and second articles 10, 20 to be recycled and to bring the polymer matrix and the polymer resin to the molten form. The temperature in the reactor may be between 50° C. and 550° C. and it may be controlled by means of temperature sensors not shown in the figure.

The depolymerization may lead to products in the form of gases which are extracted from the extruder in order to be processed. The solid residues are, for their part, removed via a suitable means 202. In particular, the reactor is capable of operating under negative pressure or under a gas stream, to convey the monomer which forms to a condensation unit via a collection means. The gases produced may be directed via a pipe 208 toward a recovery device 260 in order to be condensed. The condensate obtained may then be collected in a chamber 209 intended for this purpose.

In order to enable the recovery of gases originating from the implementation of the recycling process 100, the system 200.1 suitable for recycling may comprise one or more purification devices. For example, the system may comprise a purification device, not shown in the figures, which may correspond to a system for separation by distillation, for example a distillation column. The distillation column allows the separation of compounds as a function of their boiling point.

Another type of system that is advantageous for the recycling of a first article 10 including a composite material based on a fibrous reinforcer and a thermoplastic, preferably (meth)acrylic, polymer matrix, includes a device consisting of hollow plates heated by a heat-transfer fluid circuit (steam under pressure, oil, molten salts). In the course of its treatment, the article advances over the plates of increasing temperatures in a first stage. The solid residue ends its passage through the reactor by passing over plates which are at a lower temperature and where the heat exchange takes place from the residue to the heat-transfer fluid. The heat-transfer fluid thus heated can then serve to preheat the article at the reactor inlet.

Figure 4:
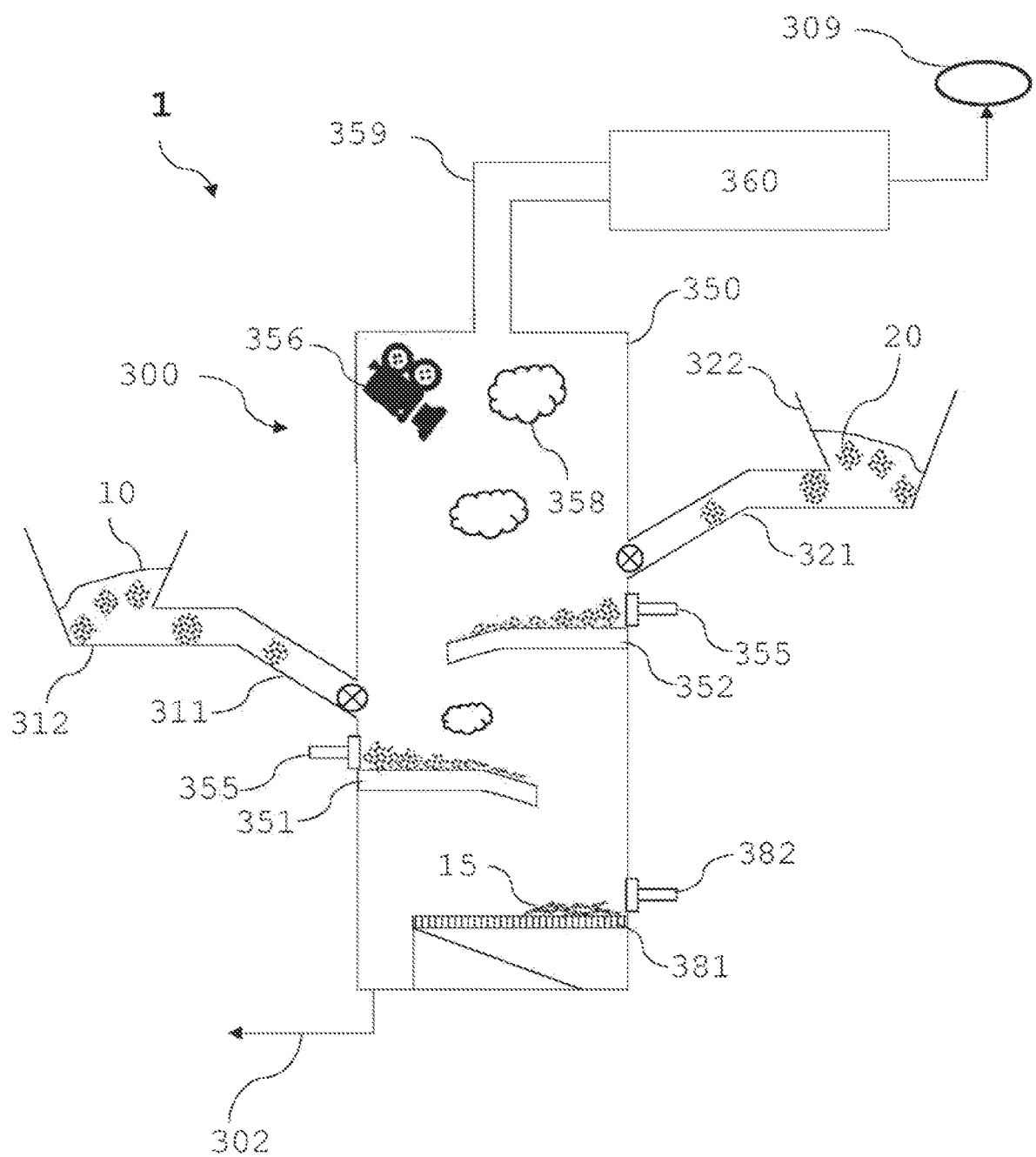
FIG. 4 represents a scheme of a side view in cross section showing an example of a recycling system including heating supports according to one embodiment of the invention.

Thus, in particular and with reference to the scheme of FIG. 4, a recycling system 300 according to the invention includes an enclosure 350 equipped with heating plates 351, 352. The system in particular includes two tanks 312, 322 for storing, respectively, the first article 10 to be recycled and the second article 20 to be recycled. These tanks are connected to the enclosure 350 via conveying pipes 311, 321 and make it possible to introduce therein said articles to be recycled, which have preferably been ground/crushed/delaminated to the appropriate particle size beforehand. As illustrated in FIG. 4, the system includes one or more heating supports 352 (such as a heating plate) onto which the second article 20 to be recycled is brought and configured to allow the temperature increase of the thermoplastic polymer, which will begin to melt under the effect of the temperature before falling onto a second heating support 351. Alternatively and according to a configuration not shown, a recycling system according to the invention is arranged so as to allow the first article 10 to be recycled to fall onto the second article 20 to be recycled, said second article to be recycled having undergone moderate heating beforehand.

In addition, the system may include a means for placing in motion 355 (for example actuated by a piston, blades or claws) arranged to push the second article 20 toward a second heating support 351. As illustrated, the second heating support 351 (such as a heating plate) is arranged so as to receive the first article 10 to be recycled and to place it in contact with the second article 20 to be recycled which is at least partially molten. In addition, the second heating support 351 is configured so as to enable the polymer matrix to depolymerize under the effect of the temperature.

In the enclosure 350, the first and second articles 10, 20 to be recycled are heated and the polymer matrix and resin are depolymerized by means of the heating supports 351, 352 at regulated temperature. The system is then configured to maintain a temperature that is high enough to depolymerize the thermoplastic polymers, preferably (meth)acrylic polymers. The temperature in the enclosure may be between 50° C. and 550° C. and it may be controlled by means of temperature sensors not shown in FIG. 4. The system may then be arranged so as to push the mixture of the first and second articles 10, 20 to be recycled toward a third heating support (or a cascade of multiple stages) or toward a separation means 381 such as a screen or a grate for separating the solid residues as a function of their diameter. Such a separation means may be used, for example, for separating the fiber residues 15 from the other fillers that may be contained in the second article 20 to be recycled. In addition, the separation means 381 may be coupled to a means for placing in motion 382 (e.g. piston, motor) for improving and/or accelerating the separation. The solid residues may then be removed via a suitable means 302.

In the reactor, the polymers, preferably meth(acrylic) polymers, are depolymerized under the action of heat to lead notably to the methyl methacrylate monomer, in the case of articles to be recycled composed of meth(acrylic) thermoplastic polymer in gas form. The gases 358 produced may be directed via a pipe 359 toward a cooling system 360 in order to be condensed. The condensate obtained may then be collected in a chamber intended for this purpose. The enclosure and the chamber are preferably under negative pressure or under a gas stream, to convey the monomer which forms to a condensation unit. The condensation unit is more particularly capable of condensing the base monomer mixture in the gaseous state. In particular, as presented previously in connection with FIG. 3, the reactor is capable of operating under negative pressure or under a gas stream, to convey the monomer which forms to a condensation unit via a collection means. In particular, the gases produced may be directed via a pipe 359 toward a recovery device 360 in order to be condensed. The condensate obtained may then be collected in a chamber 309 intended for this purpose. In order to enable the recovery of gases originating from the implementation of the recycling process 100, the system 300 suitable for recycling may comprise one or more purification devices. For example, the system may comprise a purification device, not shown in the figures, which may correspond to a system for separation by distillation, for example a distillation column. The distillation column allows the separation of compounds as a function of their boiling point.

In addition, the gases produced in the reactor may be carried to a gas/solid separator such as a cyclone. Such a separator can be internal or external to the reactor. There may also be a plurality of internal and external separators in series, the purpose of which is to recover the reinforcer particles. Thus, the solid particles entrained in the gas phase are filtered/separated either in the gas phase before the condenser or in the liquid phase after the condenser.

In a third embodiment, the system suitable for the recycling of a first article 10 including a composite material based on a fibrous reinforcer and a (meth)acrylic thermoplastic polymer matrix includes a device of mixer-conveyor type, for example a paddle dryer mixer-conveyor. This device comprises a reactor in which is placed an impeller/rotating paddle. The impeller thus enables the mixing and homogenization of a mixture of a first and a second article to be recycled. The mixer-conveyor has the advantage of enabling large amounts of solid waste/residues to be processed. It also enables good heat transfer between the wall and the waste. Such a device may be used at low temperature for drying a solid, but, in the context of the invention, by increasing the temperature, it is possible to induce depolymerization.

Figure 5:
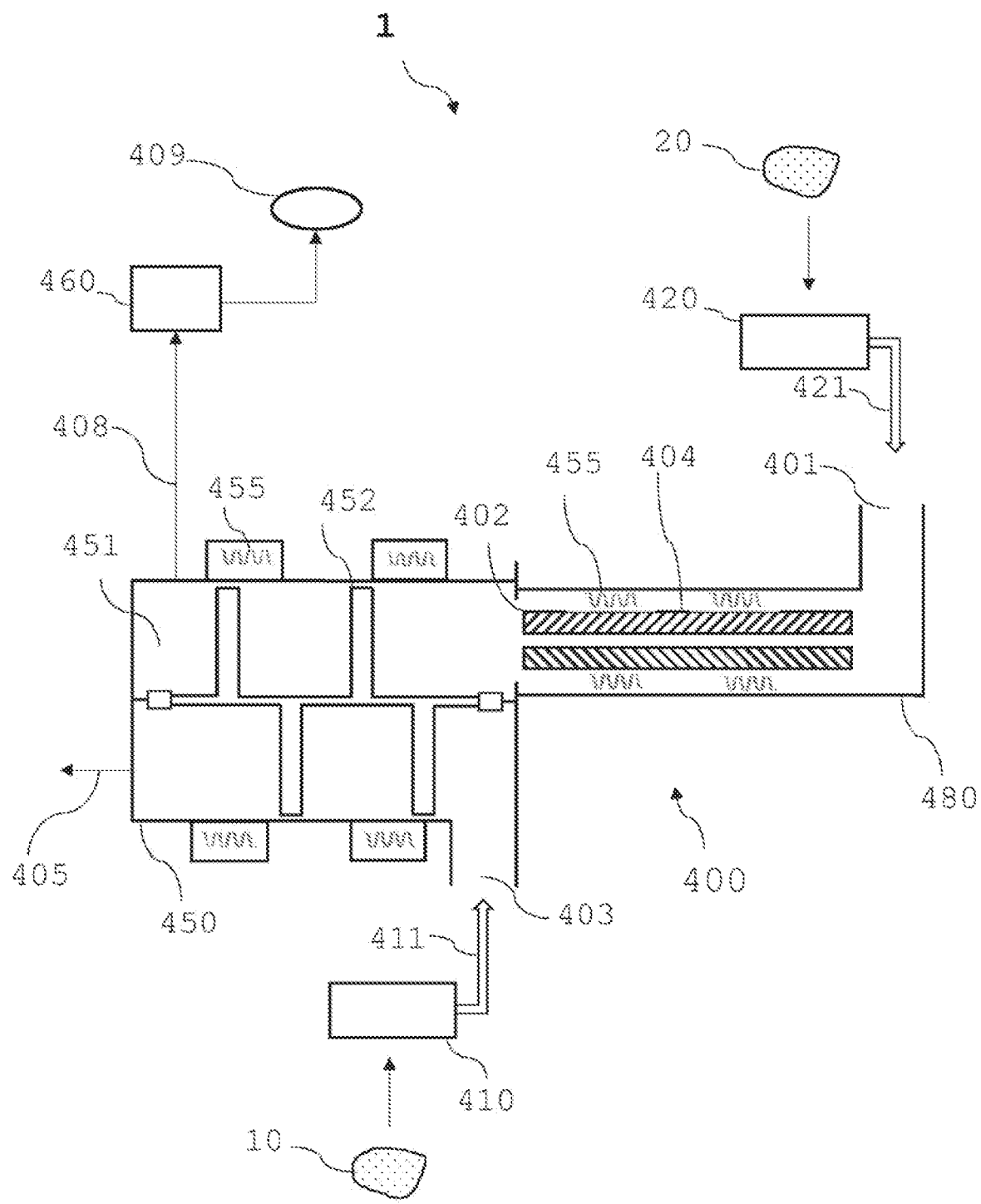
FIG. 5 represents a scheme of a top view in cross section showing an example of a recycling system including a rotating drum according to one embodiment of the invention.

A fourth embodiment of a recycling system 400 according to the invention is illustrated in FIG. 5. Such a system may comprise a device of rotating drum type in which the entire reactor is rotated on a longitudinal axis. Alternatively, the drum is fixed and it is an impeller/blade which rotates (paddle-dryer type).

The device of rotating drum type advantageously includes a reactor 450 comprising an orifice 403 via which a first article 10 to be recycled, including a composite material based on a fibrous reinforcer and a thermoplastic, preferably (meth)acrylic, polymer matrix, may be inserted, for example by means of a metering device 410 and a conveying means 411. Similarly, a second article 20 to be recycled including a thermoplastic, preferably (meth)acrylic, polymer resin may be inserted, for example by means of a metering device 420 and a conveying means 421. As described previously, a reactor of a system according to the invention may take various forms on condition that the gas streams and the temperature can be controlled; thus, a reactor of a system according to the invention may be suitable for a device of rotating drum type.

The first and second articles 10, 20 to be recycled may be in powder or granule form or may have been crushed. In this embodiment, the orifice 403 is arranged to receive the first article 10 to be recycled via the conveying means 411 of the metering device 410 and the second article 20 to be recycled via the conveying means 421 of the metering device 420.

In order to improve the yield relating to the production of base monomer from the thermoplastic polymers obtained from the articles 10, 20 to be recycled, a system 1 in accordance with the invention may comprise a second reactor 480 suitable for the moderate heating of one of the articles 10, 20 to be recycled. Advantageously, but without being limiting, such a reactor 480 may correspond to a single-screw or twin-screw extruder 200, as described in connection with FIG. 3, and comprises one or two screws 404 rotating inside said second reactor 480.

In this embodiment, the reactor 480 comprises an orifice 401 via which said first and second articles 10, 20 to be recycled may be inserted, for example via the metering devices and the conveying means mentioned previously. Preferentially, the second article 20 to be recycled is introduced via the orifice 401 of the reactor 480 and undergoes moderate heating during its passage in said reactor.

Like the heating means of the twin-screw extruder 200, an external heating means 455 regulates the temperature of the reactor 450 and is advantageously configured to heat the second article 20 to be recycled and to bring the polymeric resin into molten form without inducing depolymerization. The temperature in the reactor may be between 200° C. and 350° C. and it may also be controlled by means of temperature sensors not shown in the figure.

Such moderate heating advantageously makes it possible to liquefy all or a part of the polymer resin of the article 20 to be recycled so that said article is conveyed to the reactor 450 in the form of a viscous mixture via an orifice 402 arranged to enable fluid communication between said reactors 450 and 480. Thus, the article 10 to be recycled is preferentially added directly after introducing the article 20 to be recycled by mechanical or pneumatic transportation into the reactor 450.

In addition, the reactor 450 may comprise a motor source (not shown) driving in rotation said reactor 450 around a fixed axle 451, in the case of a rotating drum, or a rotating axle 451 in the case of a reactor 450 of a Paddle Dryer type mixer-conveyor. Such an axle 451 may advantageously comprise one or more means for placing in motion 452, or one or more mixing components, fixed along said axle. Such a means for placing in motion may advantageously take the form of a blade or an impeller, having any geometrical form suitable for mixing the articles 10, 20 to be recycled. The means for placing in motion 452 thus enables the mixing and homogenization of a mixture of a first article 10 and a second article 20 to be recycled.

A suitable means for placing in motion is chosen as a function of the nature and size of the articles 10, 20 to be recycled, which are in the form of powder or of granules.

Finally, the reactor 450 may advantageously include an external heating means 455 which regulates the temperature of the reactor 450 and which is configured to heat the articles 10, 20 to be recycled and to melt the polymer matrix of the article 10 to be recycled and the polymer resin of the article 20 to be recycled. As described previously in connection with FIG. 2, the heating may also be staged, with a first heating zone at a moderate temperature, followed by a second and last or a second and thus a plurality of heating zones at increasing temperature.

In a similar manner to system 1 described in connection with FIG. 3, the depolymerization may lead to products in gas form which are extracted from the device in order to be processed. In particular, the reactor 450 is capable of operating under negative pressure or under a gas stream, to convey the monomer which forms to a condensation unit via a collection means. The gases produced may be directed via a pipe 408 toward a recovery device 460 in order to be condensed. The condensate obtained may then be collected in a chamber 409 intended for this purpose.

The system presented in connection with FIG. 5 may also comprise a purification device, not shown in the figures, which may correspond to a system for separation by distillation, for example a distillation column, as described in connection with FIG. 3.

Thus, once the articles 10, 20 to be recycled have been introduced and placed in contact in the reactor 450, these articles undergo depolymerization, respectively, of their polymer matrix and polymer resin. Specifically, the reactor 450 also includes a heating means 455, but said heating means is advantageously configured to induce a configurable temperature, of between 200° C. and 1500° C. and suitable for inducing depolymerization of the articles 10 and 20 to be recycled. Said heating may also be staged.

Besides the fact of making it possible to homogenize said articles 10, 20 to be recycled, the means for placing in motion 452 facilitate the depolymerization of said articles in the reactor 450 by promoting their contact.

In contrast with known rotating drum systems, said system may advantageously be used in the absence of solid serving to promote the heat transfer, which is particularly suited to the recycling of composite articles.

A person skilled in the art will appreciate that the conveying means used are intrinsic to each embodiment of a recycling system in accordance with the invention and are thus notably suited to the use of a Paddle Dryer type mixer-conveyor, a rotating drum or a twin-screw extruder. Similarly, it is envisaged that each of the embodiments of a system according to the invention can comprise recovery means 405 suitable for the residues or solids derived from the depolymerized articles to be recycled.

The invention will be further illustrated by the examples that follow. However, these examples should not in any way be interpreted as limiting the scope of the present invention.

EXAMPLES

A] Preparation of Composites with Fibrous Reinforcer to be Recycled

Two composite compositions are prepared by dissolving PMMA pearls consisting of copolymers of methyl methacrylate and of an acrylate. Preferably, the acrylates will be selected from methyl acrylate, butyl acrylate and ethyl acrylate.

This type of product is commercially available, for example, from Altuglas in the Altuglas® BS range. Altuglas® PMMA or acrylic glass is typically the material which corresponds to the principle of recycling and circularity, since it has the unique feature of being able to be depolymerized to methyl methacrylate and thus of being able to be reintroduced into the process for manufacturing new resins.

A composite composition is prepared from recycled polymers. Use is made, for example, of injection-molded PMMA parts such as the rear lights of motor vehicles, or alternatively transparent plates which have served in flat-screen televisions or computer monitors. The parts are washed, dried and ground before being dissolved in methyl methacrylate.

The preparations of various composites C1, C2, C3 to be recycled illustrated in the present invention are described below.

Example 1: Composite 1 (C1)

In this example, PMMA pearls consisting of a copolymer of methyl acrylate and of methyl methacrylate (MMA) are taken. 100 g of pearls with a mean particle size of from 0.150 to 0.200 mm, a density of 0.7 g/ml and a Tg (glass transition temperature) of 107° C. are dissolved in 900 g of methyl methacrylate stabilized with 100 mg/kg of HQME (hydroquinone monoethyl ether).

10 g of benzoyl peroxide are added to the dissolved mixture.

For the preparation of the test composite, a glass fiber fabric of 600 g/m$^2$ is used. The fabric is manually impregnated with the PMMA/MMA solution. The solution is spread on the mold with a brush or a roller, and the first layer of fabric is then applied. A new layer of solution is then applied and is spread out with a roller, which also serves to remove the bubbles, and this operation is repeated until ten layers of glass fiber fabric have been applied. An absorbent tissue which will facilitate the stripping from the mold is finally put in place. The whole is placed in a plastic bag, which is placed under a partial vacuum (500 mbar, i.e. under negative pressure). The whole is then heated at 80° C. for 4 hours, and is then left to cool to room temperature.

Example 2: Composite 2 (C2)

Example 1 is repeated, but with 200 g of pearls having a Tg of 110° C., a mean particle size of from 0.150 mm to 0.200 mm and a density of 0.7 g/ml, which are dissolved in 800 g of methyl methacrylate. 10 g of benzoyl peroxide are added to the mixture. The other operations are the same as for Example 1.

Example 3: Composite 3 (C3)

In this example, use is made of 100 kg of PMMA plates obtained from the deconstruction of television and computer flat screens. This product is thus the result of production from several PMMA manufacturers, with products extending over several years of production, and of varied but mainly Asiatic origin given the nature of the products deconstructed. The plates selected are relatively clean, so as not to interfere with the test, and the edges are trimmed off so as to remove any traces of contamination with adhesives, metals and other polymers. The plates are ground into pieces about a centimeter in size and are then washed and dried. The products are then dissolved in 900 kg of methyl methacrylate. Once the dissolution is complete, the solution is filtered to remove the foreign bodies and any polymer that has not fully dissolved. 10 kg of benzoyl peroxide are then added. Composites are produced as in Example 1, so as to consume all of the solution prepared.

The composites C1, C2, C3 are ground down to maximum sizes of 2 cm.

B] Configuration of the Depolymerization Tests

1) Laboratory Test Equipment

The laboratory reactor is a batch reactor with a working volume of 4.5 liters, having a cast iron pot with a capacity of 1.2 liters and on which is mounted a removable grate, and is electrically heated from the outside. The vapors produced during the pyrolysis are condensed by means of cold traps mounted in series. The first three traps are made of stainless steel and are maintained at 5° C., 0° C. and −78° C., respectively. The last trap is made of Pyrex and is maintained at −78° C. The uncondensable gases are directed to the exterior. Once the reactor is filled, it is purged under vacuum and/or under nitrogen so as to remove the molecular oxygen from the enclosure. The tests are performed under a vacuum of about 2.5 kPa.

2) Pilot Test Equipment

The pilot tests are performed in a cylindrical reactor 3 m long and 0.6 m in diameter which is heated from the outside to avoid any condensation in the installation. The heating for the depolymerization reaction is performed by hotplates supplied with a heat-transfer fluid. The product to be depolymerized is placed on the hotplates and flows through the installation. The assembly comprises a supply system, a condensation unit, a system for discharging the solid residue and a vacuum pump. In continuous mode, the system allows a delivery of 50 kg/hour. Given the available amounts of composites, the tests were performed in a first stage in "batch" mode. In this mode, the residue supply and withdrawal systems are not used and the bed of products to be depolymerized is placed in rectangular containers on the heating plates.

The containers are filled with the product to be depolymerized, weighed and placed in the reactor. The condenser functions by spraying the pyrolysis gases and is initially charged with water. The condensation liquid circulates in the installation so as to maintain a continuous flow in the condenser. When the installation is started up, the air inside the reactor and in the peripherals is evacuated by means of the vacuum pump. The reactor is then heated to the desired temperature.

Pyrolysis in the pilot reactor is performed at 380° C.-425° C., under a pressure of 2.1 kPa. The gases produced are rapidly cooled in two condensers of spray column type in series. In the first condenser, the vapors are cooled by using a portion of the liquid condensed at the bottom and cooled with water. During the tests, the excess liquid which accumulates in the condensers is automatically evacuated into a vessel attached to each condenser. The gases exiting the first condenser enter the second condenser where they are once again placed in contact with the condensed liquid at the bottom of the condenser and cooled with water. The water condensed in this second condenser is separated out by decantation of the recovered product.

When the pyrolysis is stopped, the heating is stopped and the pressure is increased to atmospheric pressure by adding nitrogen to prevent any oxidation during the cooling of the solid.

After reaction, the residual solid mass and the masses of the collected liquids are measured to determine the mass balance.

3) Sampling Procedure

The aqueous and organic phases collected in the laboratory or pilot condensers are decanted, separated and stored in plastic vessels. Representative samples are collected after homogenization. Before analysis, the samples are stored under cold conditions and protected from light.

C] Depolymerization Tests-Laboratory Test

Example 4

200 g of Altuglas® HT121 resin granules, with a density of 1.19, are placed in the depolymerization reactor. The product is available from the company Altuglas.

Example 5

Example 4 is repeated with 200 g of Altuglas® HFI10 resin with a density of 1.15. The product is available from the company Altuglas.

A temperature increase ramp is applied to the reactor so that it reaches the nominal temperature of 400° C. in 30 minutes. After 1 hour, the heating is stopped and the temperature is returned to room temperature. The assembly is left under a stream of nitrogen at atmospheric pressure, for 2 hours after stopping the heating. Once the temperature has returned below 50° C., the traps may be removed and the masses of condensate weighed.

The polymer decomposition products are recovered for analysis. A material balance is determined. The mass of residual polymer is determined. The condensate caught in the traps is weighed. The difference in mass is attributed to the losses of light products due to cracking (methane, light hydrocarbons, CO, $CO_2$, etc.), also known as the uncondensable gases.

The condensate is notably analyzed by gas chromatography.

Examples 6 and 7

The preceding examples are repeated with 300 g of granules.

Examples 8 and 9

200 g of composites from examples 1 and 2, C1 and C2 respectively, are used, and are ground to obtain shards having a largest dimension of less than 2 cm. The ground composite is placed in the depolymerization furnace and the same protocol as in the preceding examples is applied.

Examples 10 and 11

The preceding examples are repeated with 300 g of composite.

Examples 12 to 19

Mechanical mixtures of composites and of resin granules are prepared. The mixtures are placed in plastic bags and homogenized by shaking until any visual heterogeneity is no longer distinguished. The depolymerization protocol is then repeated.

Good linearity of the decomposition products is observed for the same samples at 200 g and 300 g. In this range, the apparatus is thus not limiting in terms of heat and matter transfer.

TABLE 1

| Example | Source of PMMA | Mass | Mass of condensate | Mass of residue | Mass of MMA in the condensate | Theoretical mass of MMA | Gain obtained |
|---|---|---|---|---|---|---|---|
| 4 | Altuglas HT121 | 200 g | 135 g | 51 g | 109 g | na | na |
| 5 | Altuglas HFI 10 | 200 g | 127 g | 70 g | 101 g | na | na |
| 6 | Altuglas HT121 | 300 g | 204 g | 90 g | 165 g | na | na |
| 7 | Altuglas HFI 10 | 300 g | 192 g | 101 g | 152 g | na | na |
| 8 | Composite 1 (C1) | 200 g | 51 g | 145 g | 39 g | na | na |
| 9 | Composite 2 (C2) | 200 g | 55 g | 137 g | 44 g | na | na |
| 10 | Composite 1 (C1) | 300 g | 74 g | 221 g | 58 g | na | na |
| 11 | Composite 2 (C2) | 300 g | 77 g | 216 g | 62 g | na | na |
| 12 | HT121/C1 | 100 g/ 100 g | 100 g | 95 g | 85 g | 74 g | +14.9% |
| 13 | HT121/C2 | 100 g/ 100 g | 103 g | 90 g | 87 g | 76.5 g | +13.7% |
| 14 | HFI 10/C1 | 100 g/ 100 g | 95 g | 97 g | 81 g | 70 g | +15.7% |

TABLE 1-continued

| Example | Source of PMMA | Mass | Mass of condensate | Mass of residue | Mass of MMA in the condensate | Theoretical mass of MMA | Gain obtained |
|---|---|---|---|---|---|---|---|
| 15 | HFI 10/C2 | 100 g/ 100 g | 98 g | 96 g | 83 g | 72.5 g | +14.5% |
| 16 | HT121/C1 | 50 g/ 150 g | 85 g | 108 g | 73 g | 56.5 g | +29.2% |
| 17 | HT121/C2 | 50 g/ 150 g | 82 g | 112 g | 71 g | 60.25 g | +17.8% |
| 18 | HFI 10/C1 | 50 g/ 150 g | 77 g | 116 g | 66 g | 60 g | +10.0% |
| 19 | HFI 10/C2 | 50 g/ 150 g | 80 g | 111 g | 68 g | 63.75 g | +6.7% |

Thus, the joint recycling of a first article to be recycled including a fibrous reinforcer (C1, C2) and of a second article to be recycled including a thermoplastic, preferably (meth)acrylic polymer resin, makes it possible to significantly increase the base monomer production yields.

Thus, for the resin granule/composite mixtures, it is observed that the mass of depolymerized product (condensate) is higher than the simple addition of the masses obtained from the pure substances. It is moreover observed that the amount of MMA recovered is higher than the simple addition of the masses of MMA obtained from the pure substances, for experiments performed under the same time limits. The quality of the product recovered is thus superior for a higher productivity when mixtures of composites and of PMMA of injection molding or extrusion grades are prepared. Thus, there is indeed an increase in the mass of base monomer recovered using a process according to the invention in comparison with a mass of base monomer recovered by means of the techniques of the prior art.

C] Depolymerization Tests-Pilot Tests

Pilot Examples 20 to 23

About 20 kg of ground composite or of PMMA granules of VM100 type available from Altuglas, or a mechanical mixture of the two products, are placed in metal containers.

TABLE 2

| Example | Source of PMMA | Mass | Mass of condensate | Mass of residue | Mass of MMA in the condensate | Theoretical mass of MMA | Gain obtained |
|---|---|---|---|---|---|---|---|
| 20 | Altuglas VM100 | 20 kg | 15.1 kg | 4.7 kg | 11.9 kg | na | na |
| 21 | Composite 3 (C3) | 20 kg | 5.1 kg | 14.3 kg | 3.9 kg | na | na |
| 22 | VM100/C3 | 10 kg/ 10 kg | 11.0 kg | 8.3 kg | 8.9 kg | 7.9 kg | +12.7% |
| 23 | VM100/C3 | 5 kg/ 15 kg | 8.6 kg | 11.0 kg | 7.3 kg | 5.9 kg | +23.7 |

In the pilot tests also, it is possible to observe a significant gain in the base monomer production yield.

Thus, the present invention proposes a simple and efficient solution for increasing the overall base monomer production yield during recycling of a composite article, in particular in the case of a first article including a fibrous reinforcer and having a low monomer production yield. A process according to the invention makes it possible to perform recycling of articles comprising a composite material, the carbon footprint of which is reduced and which is therefore more environmentally friendly.

The invention claimed is:

1. A process for recycling a first article to be recycled including a composite material based on a fibrous reinforcer and a thermoplastic polymer matrix, wherein said recycling process comprises:
    introduction of the first article to be recycled into a system suitable for the recycling of thermoplastic polymer,
    introduction, into the system suitable for the recycling of thermoplastic polymer, of a second article to be recycled including a thermoplastic polymer resin, and not including any fibrous reinforcer, heating of the first article to be recycled and the second article to be recycled at a given temperature in said system suitable for recycling thermoplastic polymer, so as to depolymerize the thermoplastic polymers, and to form base monomers of said thermoplastic polymers, and recovery of the constituent base monomers of said thermoplastic polymers.

2. The recycling process as claimed in claim 1, further comprising purifying the base monomers recovered beforehand.

3. The recycling process as claimed in claim 1, further comprising a step of removing solid components produced during heating of the first article to be recycled and the second article to be recycled.

4. The recycling process as claimed in claim 1, wherein the thermoplastic polymer matrix of the first article to be recycled is a poly(methyl methacrylate) matrix.

5. The recycling process as claimed in claim 1, wherein the first article to be recycled and the second article to be recycled are introduced in a mass ratio of between 0.1 and 1.5.

6. The recycling process as claimed in claim 1, wherein the first article to be recycled has a mass percentage of fibrous reinforcer of greater than 30%.

7. The recycling process as claimed in claim 1, wherein the second article is in the form of a syrup at room temperature and has a mass percentage of equivalent thermoplastic monomer.

8. The recycling process as claimed in claim 1, wherein the second article to be recycled has a mass percentage of equivalent thermoplastic monomer.

9. The recycling process as claimed in claim 1, wherein the second article to be recycled has a mass percentage of equivalent methyl methacrylate monomer of less than 95%.

10. The recycling process as claimed in claim 1, wherein the system suitable for recycling thermoplastic polymer resin is selected from:
an extruder and/or conveyor depolymerization system,
a rotating drum depolymerization system, and
a system of depolymerization on heating plates.

11. The recycling process as claimed in claim 1, wherein during heating, the first article to be recycled and the second article to be recycled are heated to a temperature of between 200° C. and 1500° C.

12. The recycling process as claimed in claim 1, further comprising moderate heating of the thermoplastic polymers, so as to at least partially liquefy them.

13. The recycling process as claimed in claim 1, wherein said process comprises recovery of the fibrous reinforcer of the first article to be recycled, said recovery being performed by at least one of the following processes: centrifugation, draining, spinning, pressing, filtering, screening and/or cycloning.

14. The recycling process as claimed in claim 1, further comprising a preliminary sorting step.

15. The recycling process as claimed in claim 1, further comprising a grinding step.

16. The recycling process as claimed in claim 1, wherein the second article to be recycled includes at least 50 mass % of thermoplastic polymer.

17. A system for recycling a first article to be recycled including a composite material based on a fibrous reinforcer and a thermoplastic polymer matrix, wherein the system comprises:
a means for conveying said first article to be recycled,
a means for conveying a second article to be recycled including a thermoplastic polymer resin, and not including any fibrous reinforcer, and
a reactor suitable for heating the articles to be recycled and for the depolymerization of the thermoplastic polymers, and the formation of base monomers of said thermoplastic polymers.

18. The recycling system as claimed in claim 17, further comprising a second reactor suitable for moderate heating of one of the articles to be recycled, said second reactor comprising an aperture arranged to be in fluid communication with the first reactor.

19. The recycling system as claimed in claim 17, further comprising a means for recovering constituent base monomers of the thermoplastic polymers.

20. The recycling system as claimed in claim 17, further comprising a means for placing in motion said first and second articles to be recycled.

21. The recycling system as claimed in claim 17, wherein the reactor is an extruder or a conveyor.

22. The recycling system as claimed in claim 17, wherein the reactor is a pyrolysis reactor.

* * * * *